(12) United States Patent
Argentine

(10) Patent No.: US 8,585,750 B2
(45) Date of Patent: Nov. 19, 2013

(54) RETRACTION MECHANISM AND METHOD FOR GRAFT COVER RETRACTION

(75) Inventor: Jeffery Argentine, Petaluma, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 734 days.

(21) Appl. No.: 12/763,920

(22) Filed: Apr. 20, 2010

(65) Prior Publication Data

US 2011/0257719 A1  Oct. 20, 2011

(51) Int. Cl.
*A61F 2/06* (2013.01)

(52) U.S. Cl.
USPC ........................................................ 623/1.12

(58) Field of Classification Search
USPC ............. 623/1.11, 1.12, 1.13, 1.2, 1.23, 2.11; 606/108, 139, 153
See application file for complete search history.

(56) References Cited

U.S. PATENT DOCUMENTS

| | | |
|---|---|---|
| 5,906,619 A | 5/1999 | Olson et al. |
| 6,203,550 B1 | 3/2001 | Olson |
| 6,911,039 B2 | 6/2005 | Shiu et al. |
| 7,105,016 B2 | 9/2006 | Shiu et al. |
| 7,491,501 B2 | 2/2009 | Wooten |
| 2004/0127912 A1* | 7/2004 | Rabkin et al. ................. 606/108 |
| 2005/0080476 A1 | 4/2005 | Gunderson et al. |
| 2006/0229561 A1* | 10/2006 | Huszar ..................... 604/164.01 |
| 2008/0262590 A1 | 10/2008 | Murray |

FOREIGN PATENT DOCUMENTS

EP   1358903   11/2003

* cited by examiner

*Primary Examiner* — Ryan Severson
*Assistant Examiner* — Rachel S Papeika

(57) ABSTRACT

A stent or stent-graft delivery system includes a handle having a graft cover retractor having a screw gear and a drive and quick release assembly. The drive and quick release assembly allows a user to retract a graft cover by rotating the assembly in a first rotational direction about the screw gear. When the assembly is being rotated in a particular rotational direction, a partial revolution in the opposite rotational direction disengages the assembly from the screw gear, which is sensed by a change in the force required to rotate the assembly. With the assembly disengaged from the screw gear, the assembly can be slid along the screw so that the graft cover can be positioned more quickly. In transitioning from using the screw gear to sliding along screw gear, it unnecessary to push any button and unnecessary for the user to remove her/his hand from the assembly.

18 Claims, 16 Drawing Sheets

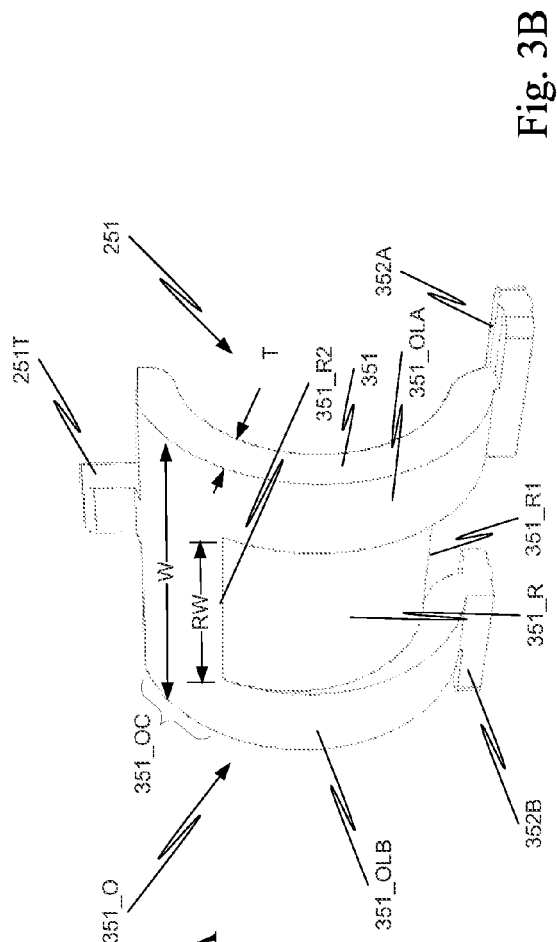
Fig. 3C
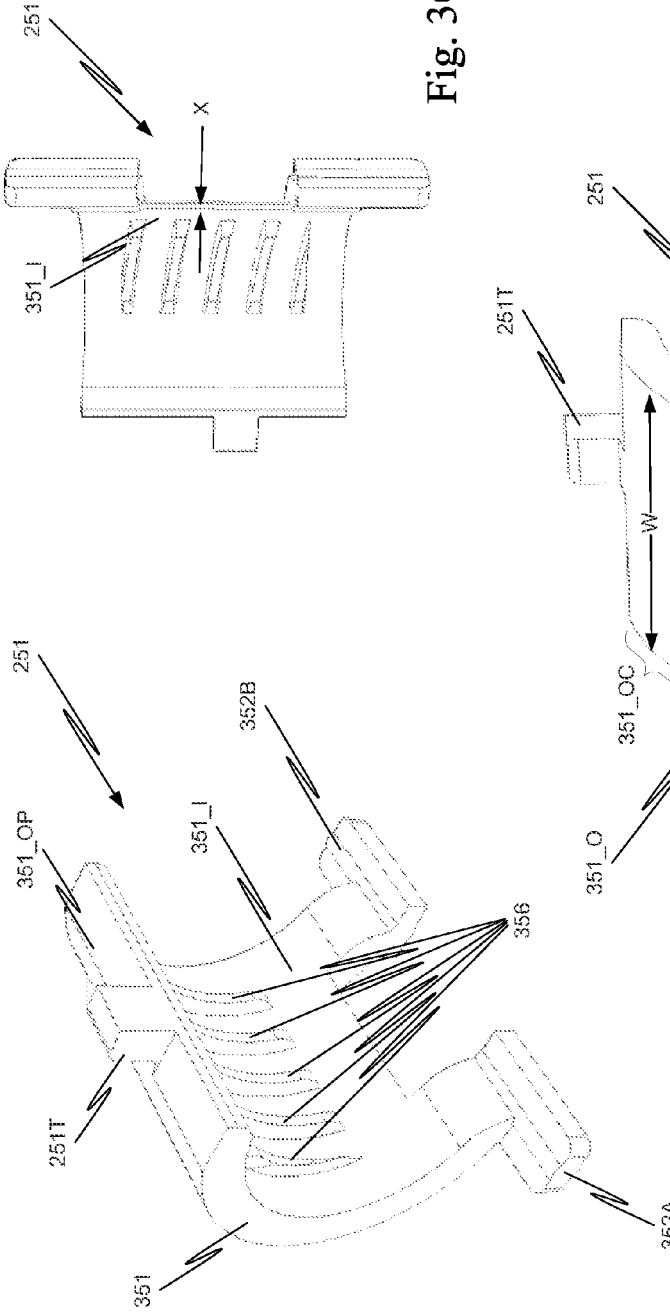
Fig. 3B
Fig. 3A

RETRACTION MECHANISM AND METHOD FOR GRAFT COVER RETRACTION

BACKGROUND

1. Field of Invention

This invention relates generally to medical devices and procedures, and more particularly to a method and system of deploying a self expanding prosthesis like a stent graft or a stent in a vascular system.

2. Related Art

Prostheses for implantation in blood vessels or other similar organs of the living body are, in general, well known in the medical art. For example, prosthetic vascular grafts formed of biocompatible materials (e.g., Dacron or expanded polytetrafluoroethylene (ePTFE) tubing) have been employed to replace or bypass damaged or occluded natural blood vessels.

A graft material supported by a framework is known as a stent-graft or endoluminal graft. In general, the use of stents and stent-grafts for treatment or isolation of vascular aneurysms and vessel walls which have been thinned or thickened by disease (endoluminal repair or exclusion) is well known.

Many stents and stent-grafts are "self-expanding", i.e., inserted into the vascular system in a compressed or contracted state, and permitted to expand upon removal of a restraint. Self-expanding stents and stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent or self-expanding stent-graft is typically configured in a tubular shape of a slightly greater diameter than the diameter of the blood vessel in which the stent or stent-graft is intended to be used. In general, rather than by treatment in a traumatic and invasive manner using open surgery, when stents and stent-grafts are used for treatment, the stent or stent-graft typically is deployed through a less invasive intraluminal delivery, i.e., cutting through the skin to access a lumen or vasculature or percutaneously via successive dilatation, at a convenient (and less traumatic) entry point, and routing the stent or stent-graft through the lumen to the site where the prosthesis is to be deployed.

Intraluminal deployment in one example is effected using a delivery catheter with coaxial inner tube, sometimes called an inner tube (plunger), and an outer tube, sometimes called the sheath, arranged for relative axial movement. The stent or stent-graft is compressed and disposed within the distal end of the sheath in front of the inner tube.

The catheter is then maneuvered, typically routed though a vessel (e.g., lumen), until the end of the catheter containing the stent or stent-graft is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent or stent-graft is gradually exposed. The exposed portion of the stent or stent-graft radially expands so that at least a portion of the expanded portion is in substantially conforming surface contact with a portion of the interior of the blood vessel wall.

The proximal end of the stent or stent-graft is the end closest to the heart by way of blood flow path whereas the distal end of the stent or stent-graft is the end furthest away from the heart by way of blood flow path during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the stent-graft is the end nearest the operator (the end nearest the handle or the handle itself), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the distal and proximal end descriptors for the stent-graft and delivery system description may be consistent or opposite in actual usage.

Some self-expanding stent deployment systems and stent-graft deployment systems are configured to have each exposed increment of the stent or stent graft at the proximal end of the stent-graft deploy (flare out or mushroom) as the sheath is pulled back. Thus, a surgeon must carefully and deliberately apply a controlled force to retract the sheath in a controlled and predictable manner.

SUMMARY

In one example, a stent or stent-graft delivery system includes a graft cover retractor. The graft cover refractor includes a screw gear including at least one longitudinal slot, and a drive and quick release assembly coupled to the screw gear.

The drive and quick release assembly slides along the at least one longitudinal slot to retract a graft cover affixed to the drive and quick release assembly. The drive and quick release assembly also rotates in a first rotational direction about the screw gear to retract the graft cover using the screw gear. The drive and quick release assembly transitions from retraction using the engagement with the screw gear to retraction by sliding by rotating the drive and quick release assembly a fraction of a complete revolution in a second rotation direction that is opposite to the first rotation direction being used to retract the graft cover.

The transition from using engagement with the screw gear to sliding retraction does not require the use of button; does not require looking away from a viewing screen; and does not require removing the hand from the drive and quick release assembly. Thus, the graft cover retractor eliminates cumbersome steps required in the operation of some conventional graft cover retraction assemblies.

In one example, the drive and quick release assembly includes a housing, and a drive mechanism mounted in the housing. The drive mechanism engages with the screw gear upon the housing being rotated a predetermined fraction of a revolution in one of the first rotational direction and the second rotational direction. The drive mechanism continues to engage the screw gear until the housing is rotated in the other of the first rotational direction and the second rotational direction.

In this example, the drive mechanism includes a graft cover anchor and a rotation drive assembly. The graft cover anchor includes a body; at least one graft cover control engagement tab positioned outside the screw gear; and a leg extending from the at least one graft cover control engagement tab through the at least one longitudinal slot in the screw gear to the body of the graft cover anchor.

The rotation drive assembly, following engagement with the screw gear and continued rotation of the housing, moves the housing along the screw gear, which in turn moves the graft cover anchor longitudinally. The rotation drive assembly releases engagement with the screw gear following the housing being rotated in the other of the first direction and the second direction until a force required for the rotation changes. Longitudinal motion of the housing along the screw gear, following the housing being rotated in the other of the first direction and the second direction, moves the graft cover anchor longitudinally.

The rotation drive assembly includes a plurality of pawls. Each pawl has an inner surface including a plurality of gear teeth for engaging with the screw gear. Each pawl also has an outer surface having a ramp surface. Finally, each pawl includes a drive pad.

The housing includes a drive rib. The plurality of gear teeth of a pawl engages the screw gear when the drive pad of the pawl is in contact with the drive rib. Conversely, the plurality of gear teeth of the pawl is disengaged from the screw gear when the drive rib is not in contact with an outer surface of the pawl.

A drag clutch further includes a first side surface, a second side surface removed from the first side surface, and an outer surface connecting the first side surface to the second side surface. The outer surface includes a release surface. The release surface includes a transition surface and a no contact surface.

The first drag clutch also includes a slot, extending through the first draft clutch from the first side surface to the second side surface. The slot has a longitudinal axis. The longitudinal axis forms an angle with a center line of the drag clutch. The angle is less than eighty degrees. The drag clutch is made of an elastomeric material.

A method of operating a graft delivery system includes rotating a drive and quick release assembly in a first rotational direction along a screw gear to move a graft cover in a first direction. The method further includes rotating the drive assembly a partial revolution in a second rotational direction opposite to the first rotation direction to disengage the from the screw gear. Next, in the method, the drive and quick release assembly is slid along the screw gear.

BRIEF DESCRIPTION OF THE DRAWINGS

FIG. 3A is an oblique view of a first pawl including an inner surface of a body of the first pawl.

FIG. 3B is an oblique view of the first pawl including an outer surface of the body.

FIG. 3C is a bottom view of FIGS. 3A and 3B.

Figure 1:
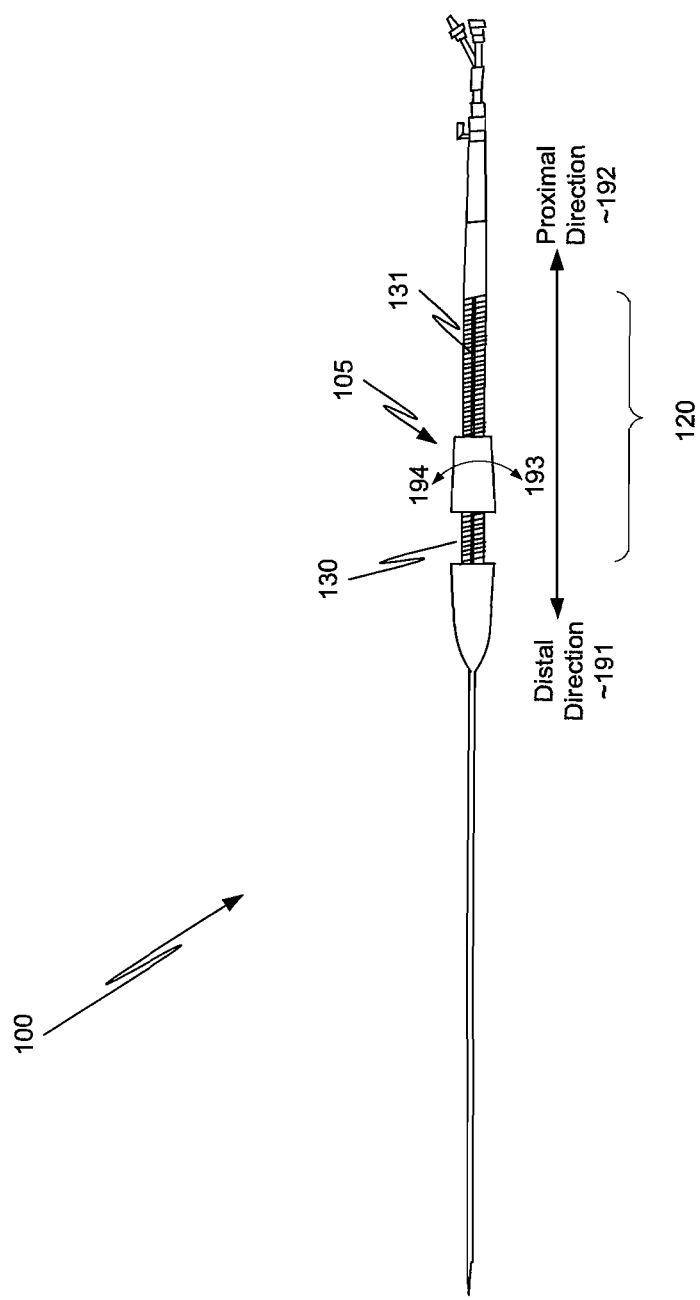
FIG. 1 is an illustration of delivery system that includes a graft cover refractor.

In the drawings, the first digit of a reference number for an element indicates the figure in which the element with that reference number first appeared.

DETAILED DESCRIPTION

Present technology for retracting a graft cover during deployment of a stent graft is adequate and functional. However, typically the conventional mechanism used in retracting the graft cover is complicated and expensive. Stent graft delivery system 100 includes a handle having a graft cover retractor 120, which overcomes these limitations.

In this example, graft cover retractor 120 includes a screw gear 130 and a drive and quick release assembly 105, sometimes referred to herein as assembly 105. A distal end of screw gear 130 is fixedly attached to a distal end of the handle, while a proximal end of screw gear 130 is fixedly attached to a proximal end of the handle.

As explained more completely below, drive and quick release assembly 105 allows a user to retract a graft cover by rotating drive and quick release assembly 105 in a first rotational direction 193 about screw gear 130, e.g., counterclockwise. The rotation of drive and quick release assembly 105 in first rotational direction 193 causes drive and quick release assembly 105 to engage screw gear 130 and then to move longitudinally along the threads of screw gear 130 in proximal direction 192. The rotation of drive and quick release assembly 105 around screw gear 130 causes the graft cover connected to assembly 105, sometimes called a sheath, to be retracted.

Conversely, to move the graft cover in distal direction 191, assembly 105 is rotated in a second rotational direction 194, which is opposite to first rotational direction 193, e.g., clockwise. The rotation of assembly 105 in second rotational direction 194 causes assembly 105 to engage screw gear 130 and then to move longitudinally along the threads of screw gear 130 in distal direction 191.

When assembly 105 is being rotated in a particular rotational direction, a partial revolution of assembly 105 in the opposite rotational direction disengages assembly 105 from screw gear 130. The disengagement is sensed by a change in the force required to rotate assembly 105. With assembly 105 disengaged from screw gear 130, assembly 105 can be slid along screw gear 130 without engaging the threads of screw gear 130 so that the graft cover can be longitudinally positioned more quickly than is possible using screw gear 130.

In transitioning from using (engagement with) screw gear 130 to sliding along screw gear 130, it unnecessary to push any button and unnecessary for the user to remove her/his hand from assembly 105. Thus, the user does not have to look away from a viewing screen to see how to manipulate delivery system 100 to change modes of graft cover retraction. The user's hand never changes position whether retracting the graft cover, i.e., whether pulling the graft cover back in a quick-retraction mode, or whether re-advancing the graft cover employing the mechanical advantage of the associated screw.

Figure 2A:
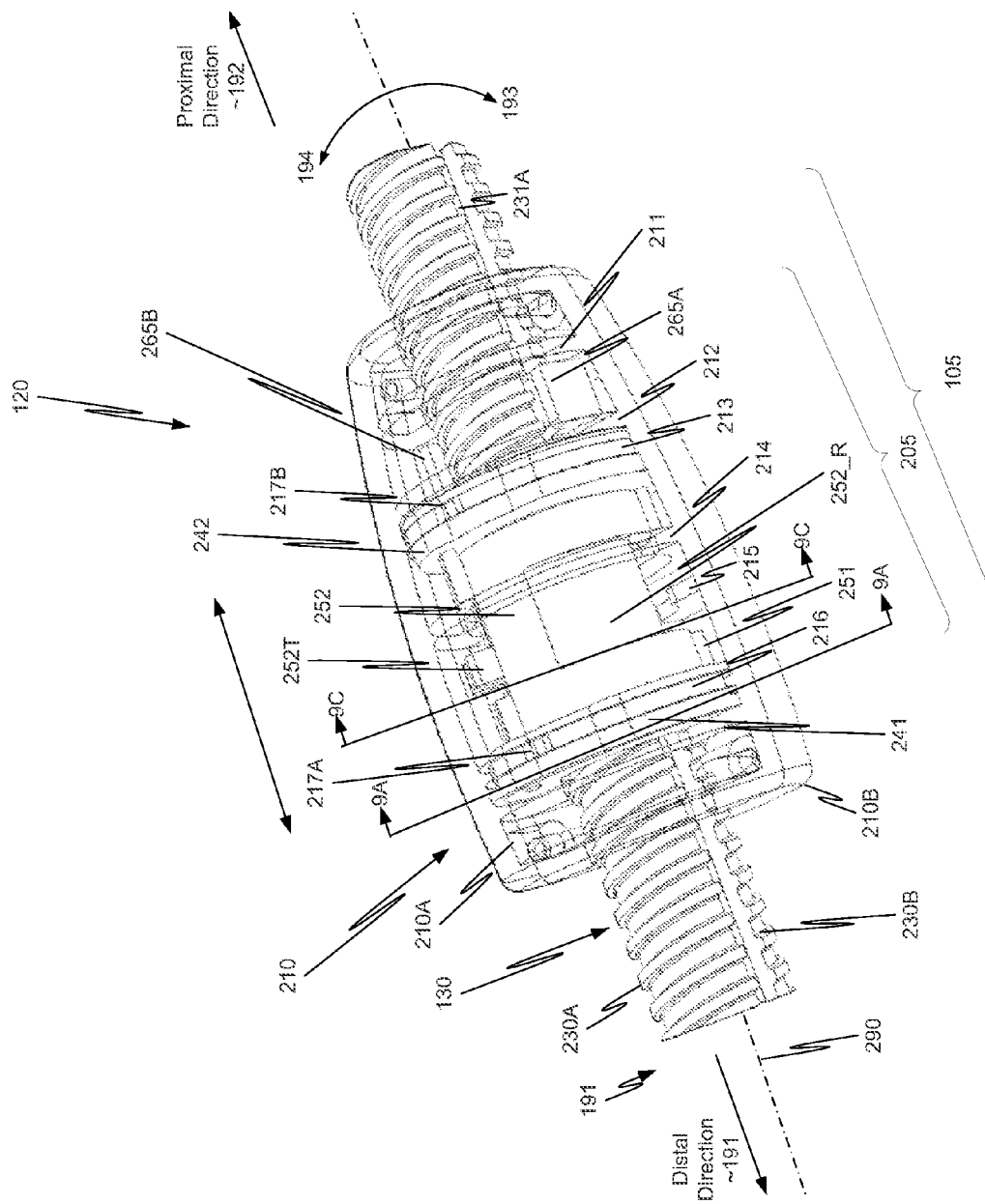
FIG. 2A is a close-up partial see through illustration of the graft cover retractor of FIG. 1.

FIG. 2A is a close-up illustration of graft cover refractor 120. Housing 210 of drive and quick release drive and quick release assembly 105 has two parts: a first housing part 210A and a second housing part 210B. In FIGS. 2A to 2E, the graft cover is not illustrated to improve clarity. The graft cover would extend from the graft cover anchor, which is described more completely below, through the interior of screw gear 130 and out the distal end of the handle to the stent or stent-graft.

First housing part 210A is illustrated as a see through frame to illustrate features within drive and quick release assembly 105. However, in other examples first housing part 210A is opaque (See FIG. 1). The transparency of first housing part 210A is for ease of discussion only and is not limiting on the characteristics of first housing part 210A. Housing 210 is made from a polymer.

In this example, drive and quick release assembly 105 includes a drive mechanism 205 that is mounted within housing 210. Drive mechanism 205 includes a graft cover anchor 260 (See FIG. 8) and a rotation drive assembly 220 (See FIG. 6). Rotation drive assembly 220 is disengaged from screw gear 130 in FIG. 2A. Graft cover anchor 260 includes graft cover control engagement tabs 265A, 265B.

A first leg of graft cover anchor 260 extends from a body of anchor 260 through a first slot 231A between a first screw gear part 230A and a second screw gear part 230B to graft cover control engagement tab 265A. While it is not visible in FIG. 2A, a second leg of graft cover anchor 260 extends from the body of anchor 260 through a second slot 231B (not shown) between first screw gear part 230A and second screw gear part 230B to graft cover control engagement tab 265B. Tabs 265A and 265B are contained in a volume within housing 210 by ribs 211, 212.

In the position illustrated in FIG. 2A, drive mechanism 205 is shown disengaged from screw gear 130. With drive mechanism 205 disengaged from screw gear 130, housing 210 can be moved along longitudinal axis 290 in either proximal direction 192 or distal direction 191.

For example, when housing 210 is moved in proximal direction 192, rib 212 contacts tabs 265A, 265B. Rib 212 transfers the longitudinal motion (force) of housing 210 to graft cover anchor 260, which in turn transfers the longitudinal motion (force) to the graft cover. Herein, longitudinal motion is linear motion along a longitudinal axis, as opposed to rotational motion about the longitudinal axis.

When housing 210 is rotated in (second) rotational direction 194 (instead of being moved along longitudinal axis 290 in proximal direction 192), a drive rib 215, which extends only partially around the inner circumferential surface of second housing part 210B (as seen in the lower part of housing 210B), rotates upward in FIG. 2A. As drive rib 215 rotates, drive rib 215 contacts a ramp surface 252_R of a second pawl 252. As drive rib 215 moves up ramp surface 252_R, drive rib 215 moves second pawl 252 radially inward towards longitudinal axis 290.

As second pawl 252 moves radially inward, a plurality of gear teeth 456 on an inner surface of second pawl 252 (See FIG. 4A.) engages with screw gear 130. As drive rib 215 is turned further, drive rib 215 leaves ramp surface 252_R and moves onto the full thickness (height) outer surface of second pawl 252. In this position, plurality of gear teeth 456 of second pawl 252 is engaged with screw gear 130 and consequently, drive mechanism 205 is engaged with screw gear 130.

When drive rib 215 contacts drive pad 252T of second pawl 252, the rotational motion of housing 210 is transferred to second pawl 252. Consequently, drive and quick release assembly 105 moves distally along longitudinal axis 290 as housing 210 is rotated about and along screw gear 130. The distal motion of housing 210 causes rib 211 to contact tabs 265A, 265B of graft cover anchor 260 so that the graft cover is moved distally.

Figure 2B:
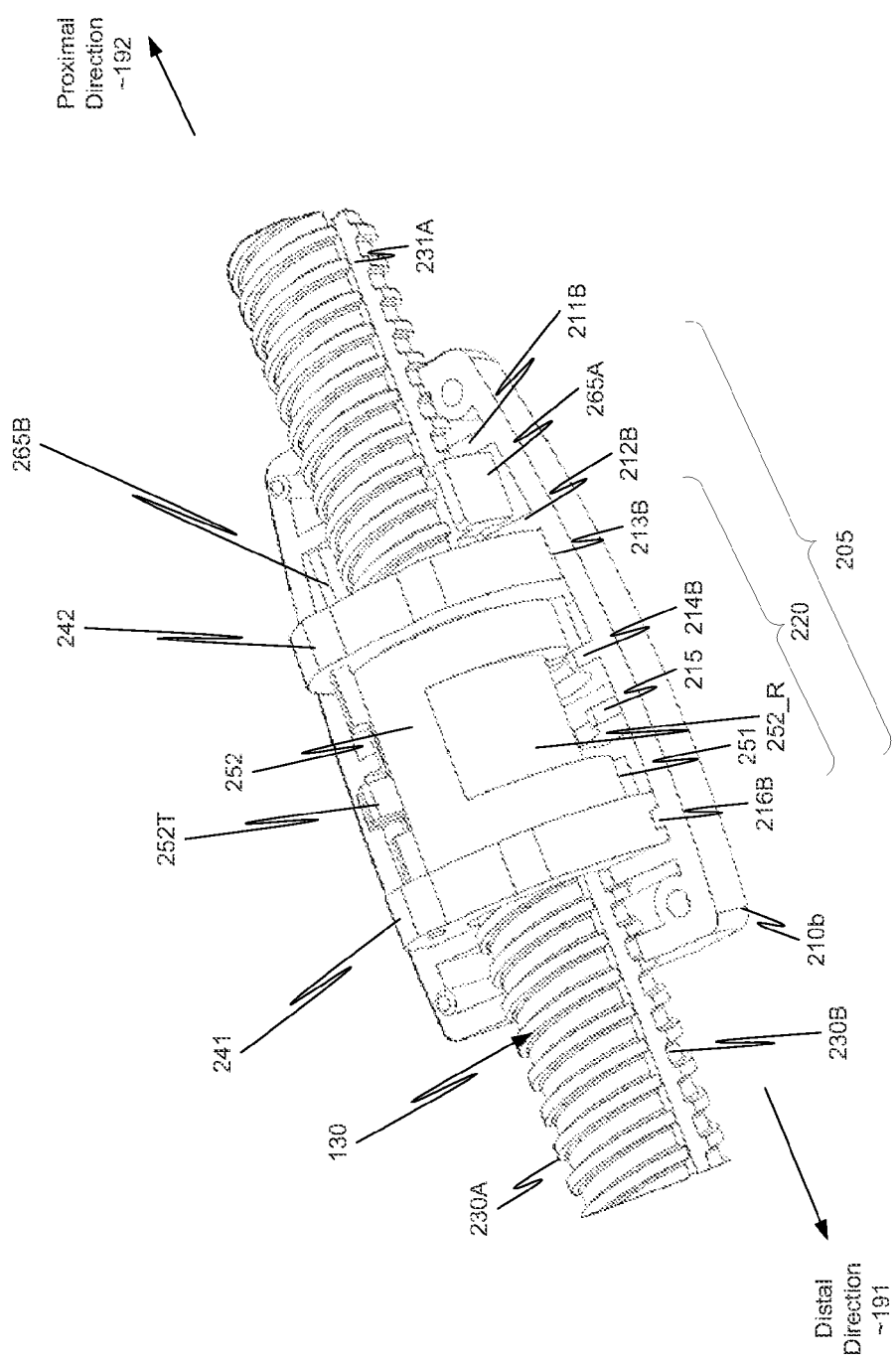
FIG. 2B is a close-up illustration of the graft cover retractor of FIG. 2A with a first housing part removed from FIG. 2A.

FIG. 2B shows first housing part 210A having been removed from FIG. 2A. Rotation drive assembly 220 includes first drag clutch 241, first pawl 251, second pawl 252, and second drag clutch 242. As explained more completely below, first pawl 251 and second pawl 252 are operatively mounted in first drag clutch 241 and second drag clutch 242.

Figure 2C:
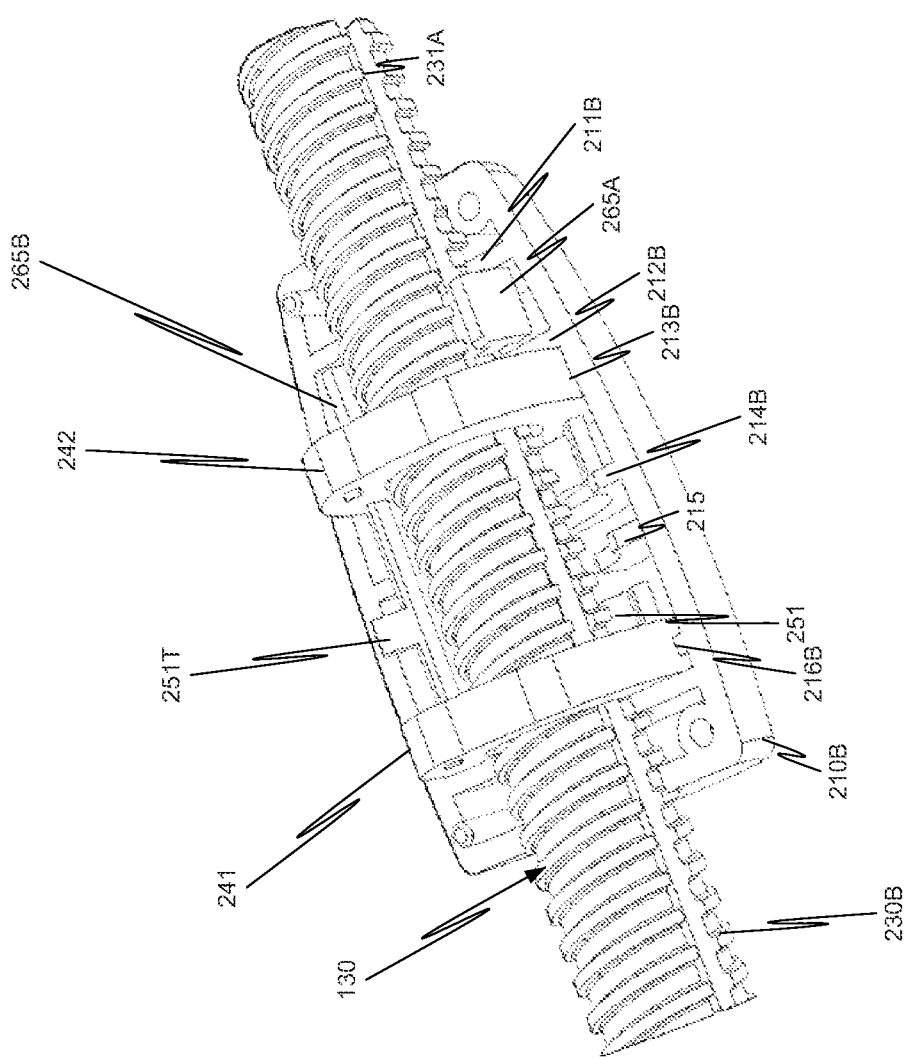
FIG. 2C is a close-up illustration of the graft cover retractor of FIG. 2A with the first housing part and a pawl removed from FIG. 2A.

FIG. 2C shows second pawl 252 having been removed from FIG. 2B. First pawl 251 with drive pad 251T is now more visible as is the portion of screw gear 130 within rotation drive assembly 220.

Figure 2D:
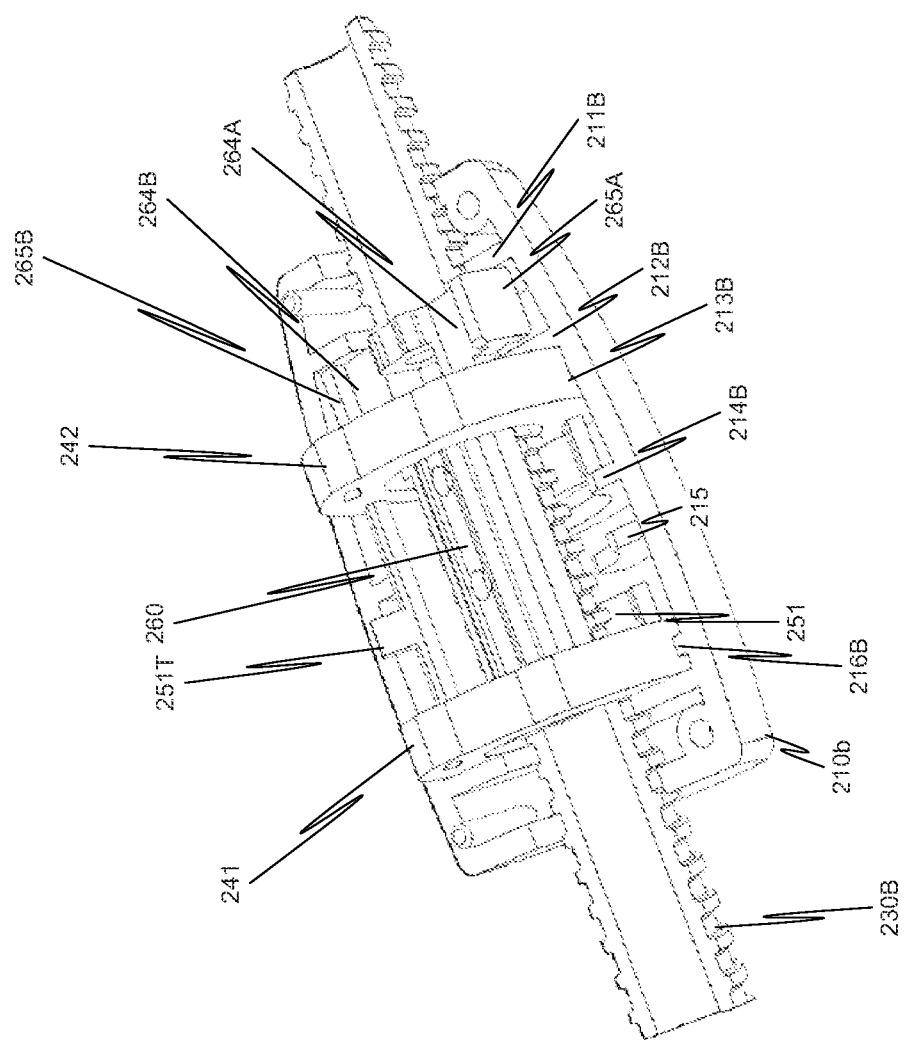
FIG. 2D is a close-up illustration of the graft cover retractor of FIG. 2A with the first housing part, the pawl and a part of the screw gear removed from FIG. 2A.

FIG. 2D shows first screw gear part 230A (half) having been removed from FIG. 2C to expose graft cover anchor 260 and legs 264A, 264B of graft cover anchor 260. Graft cover anchor 260 is described more completely below with respect to FIG. 8.

Figure 2E:
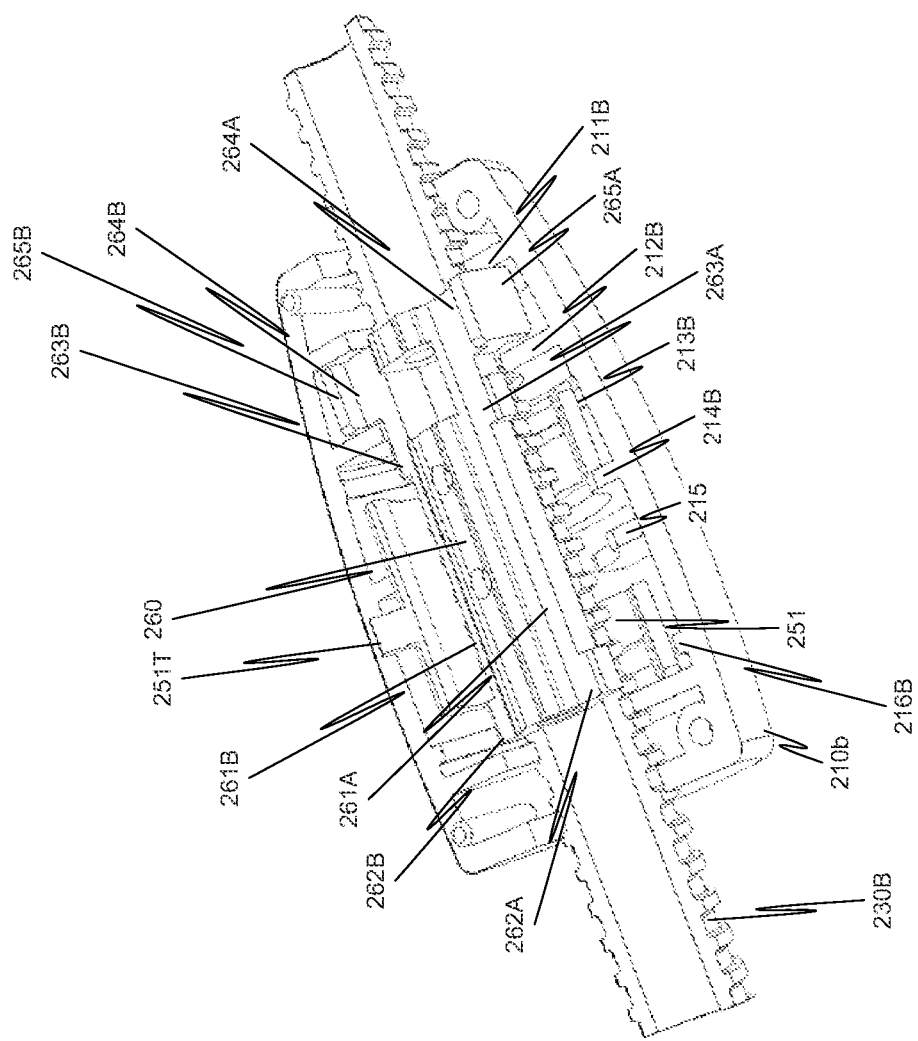
FIG. 2E is a close-up illustration of the graft cover retractor of FIG. 2A with the first housing part, the pawl the part of the screw gear, a first drag clutch and a second drag clutch removed from FIG. 2A.

FIG. 2E shows first drag clutch 241 and second drag clutch 242 having been removed from FIG. 2D to further expose graft cover anchor 260. Graft cover anchor 260 includes a first spacer 261A, a second spacer 261B, two sets of legs (262A, 262B), (263A, 263B). First spacer 261A has a width that fills first slot 231A in screw gear 130, while second spacer 261B has a width that fills second slot 231B (see FIG. 9A) in screw gear 130. Thus, first spacer 261A and second spacer 261B maintain a minimum spacing between first screw gear part 230A and second screw gear part 230B and prevents them from flexing (or bending) toward one another as the pawls and the gear teeth in the pawls are forced toward and in contact with the threads on the screw gear so that as rotation drive assembly 220 is rotated about screw gear 130 or slid longitudinally along screw gear 130, the spacing between screw gear parts 230A, 230B is maintained.

The top (outer) edge surface of each leg in a set (262A, 262B), (263A, 263B) is rounded and the distance between the top edge surfaces of a set of legs is greater than the inner diameter (inner circumferential surface 542) of a drag clutch. The drag clutch rides on the top edge surfaces of the set of legs (262A, 262B), (263A, 263B). This arrangement causes the legs to have an elastic rotational friction creating interference fit between the drag clutch inner circumferential surface 542 and the top edge surfaces of the set of legs.

First Pawl 251

FIG. 3A is a first side oblique view of first pawl 251 including inner surface 351_I of body 351. FIG. 3B is a second side oblique view of first pawl 251 including outer surface 351_O of body 351. FIG. 3C is a bottom view of first pawl 251 of FIGS. 3A, 3B. Herein, use of bottom, top, etc. is for ease of reference with respect to the drawings and is not intended to be limiting.

A portion of body 351 of first pawl 251, inner surface 351_I, is semi-cylindrical. A plurality of gear teeth 356 extends radially inward from inner surface 351_I.

Drive pad 251T extends radially outward from a planar outer surface 351_OP of body 351. Clutch engagement tabs 352A, 352B extend from a portion of body 351 on the opposite side of the arc of the pawl and removed from planar outer surface 351_O. Clutch engagement tabs 352A, 352B extend longitudinally away from body 351.

Outer surface 351_O includes planar outer surface 351_OP and also extends in an arc from an edge of planar outer surface 351_O along two leg surfaces 351_OLA and 351_OLB to terminate at a surface of clutch engagement tabs 352A, 352B. In addition to planar outer surface 351_OP, outer surface 351_O includes a contact surface 3510C, ramp surface 351_R, and two leg surfaces 351_OLA and 351_OLB.

Ramp surface 351_R is part of outer surface 351_O positioned between leg surfaces 351_OLA and leg 351_OLB. Ramp surface 351_R has a first edge 351_R1 substantially parallel to, opposite from the other end of the arc of the pawl, and radially displaced from planar outer surface 351_OP. Edge 351_R1 is radially displaced from inner surface 351_I by a distance X (FIG. 3C). Distance X is less than a thickness T of body 351. The radial distance from the centerline of the semi-cylindrical inner surface 351_I of the pawl to the ramp surface 351_R gradually increases when swinging the arc along the surface from first edge 351_R1 to second end 351_R2, where ramp surface 351_R meets and merges into contact surface 351_OC. A width RW of ramp 351_R is less than width W of body 351. Here, substantially parallel means parallel to within manufacturing tolerances.

Second Pawl 252

Figures 4A, 4B:
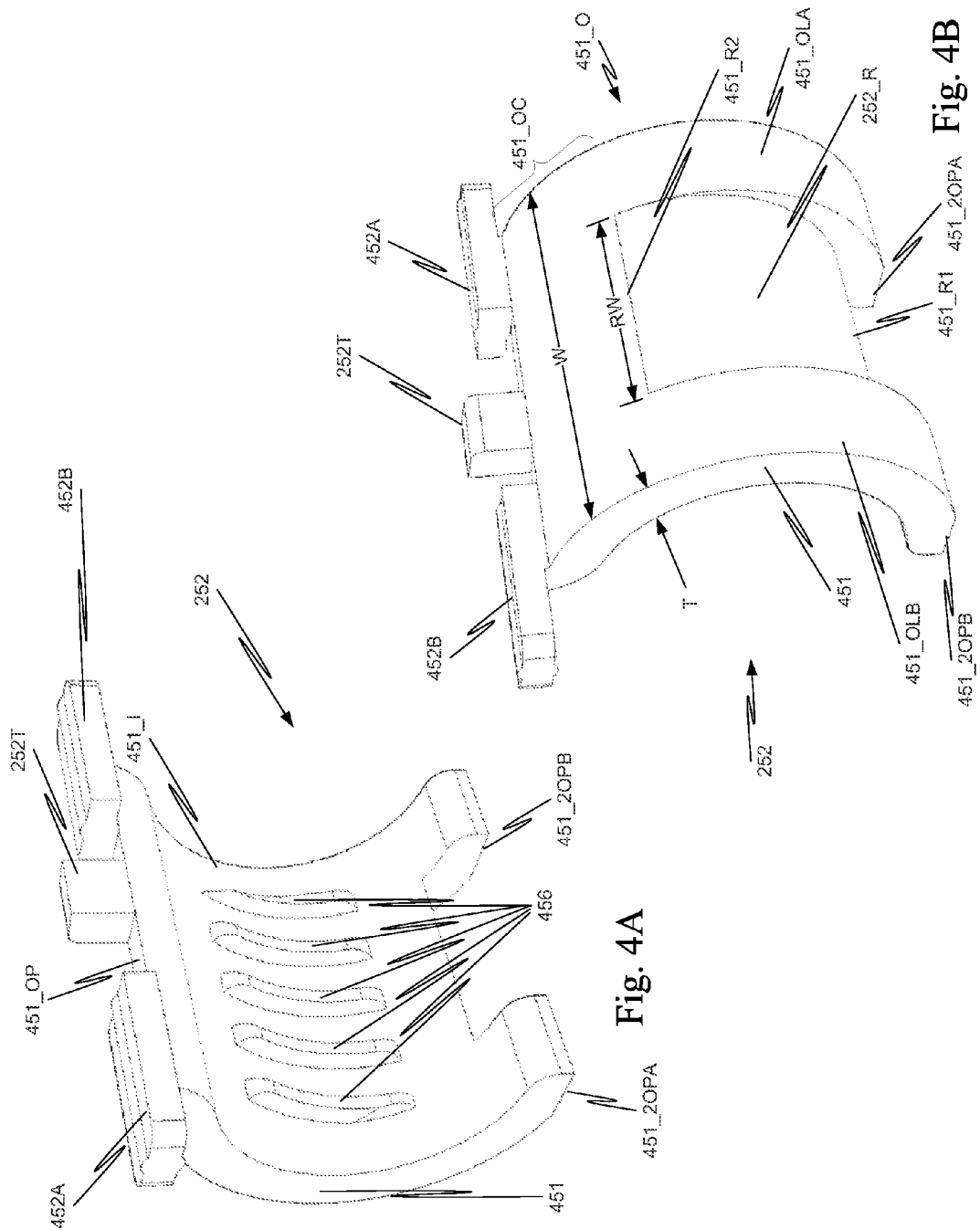
FIG. 4A is an oblique view of a second pawl including an inner surface of a body of the second pawl.
FIG. 4B is an oblique view of the second pawl including and outer surface of the body.

FIG. 4A is an oblique view of second pawl 252 including inner surface 451_I of body 451. FIG. 4B is an oblique view of second pawl 252 including outer surface 451_O of body 451. Herein, use of bottom, top, up, down, etc. is for ease of reference with respect to the drawings and is not intended to be limiting.

A portion of body 451 of second pawl 252 inner surface 451_I is a semi-cylindrical. A plurality of gear teeth 456 extends radially inward from inner surface 451_I.

Drive pad 252T extends radially outward from a first planar outer surface 451_OP of body 451. Clutch engagement tabs 452A, 452B extend longitudinally away from body 451 and from planar outer surface 451_OP.

In addition to first planar outer surface 451_OP, outer surface 451_O includes a contact surface 451_OC, ramp surface 252_R, and two leg surfaces 451_OLA and 451_OLB. Outer surface 451_O also includes two second planar surfaces 451_2OPA, 451_2OPB on the opposite side of the pawl and removed from planar surface 451_OP.

Ramp surface 252_R is part of outer surface 451_O positioned between leg surface 451_OLA and leg surface 451_OLB. Ramp surface 252_R has a first edge 451_R1 substantially parallel to, opposite on the other side of the arc of the pawl, and radially displaced from planar outer surface 451_OP. Edge 451_R1 is radially displaced from inner surface 451_I by a distance X. Here, distance X is the same distance as distance X in FIG. 3C. Distance X is less than a thickness T of body 451. The radial distance from the centerline of the semi-cylindrical inner surface 351_I of the pawl to the ramp surface 252_R gradually increases when swinging the arc along the surface from first edge 451_R1 to second end 451_R2, where ramp surface 252_R meets and merges into contact surface 451_OC. A width RW of ramp 252_R is less than width W of body 451. Again, substantially parallel means parallel to within manufacturing tolerances.

In this example, thickness T of body 451 and thickness T of body 351 are the same value, i.e., the thickness of both bodies is the same. Also, in this example, width W of body 451 and width W of body 351 are a same width. Similarly, width RW of ramp surface 252_R and width RW of ramp surface 351_R are a same width.

Drag Clutch

Figure 5A:
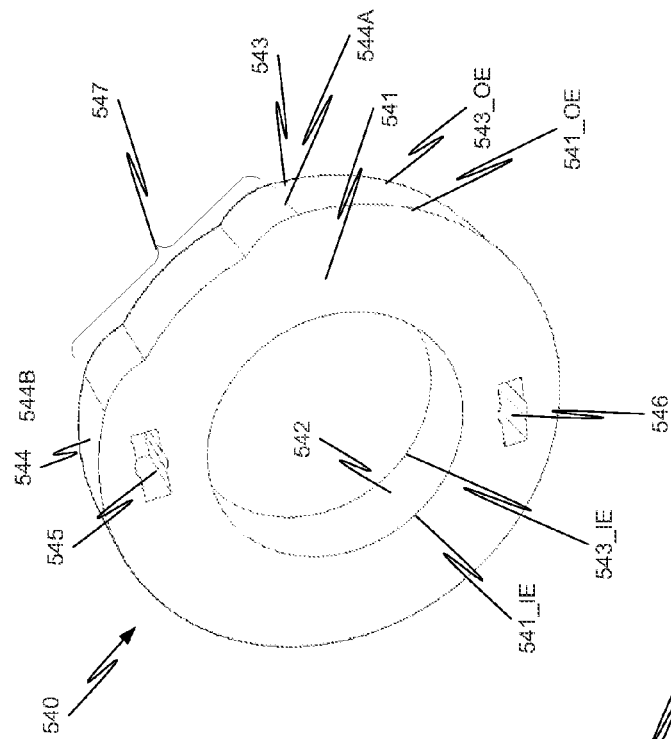
FIG. 5A is a close-up oblique view of a drag clutch.
Figure 5B:
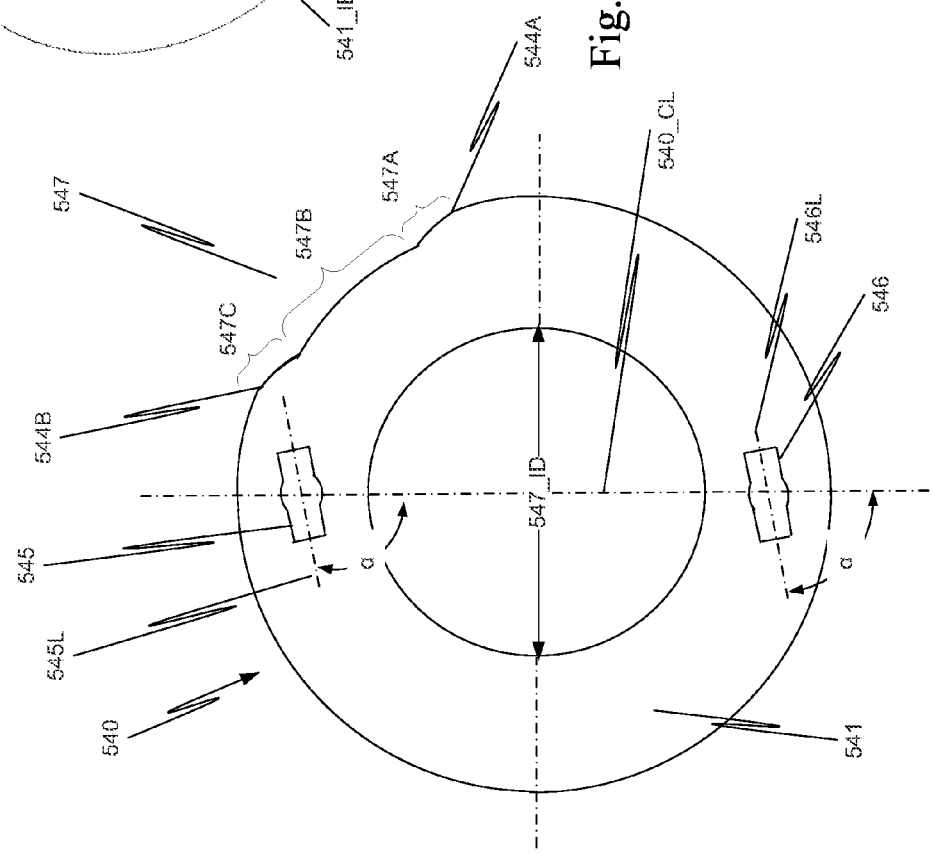
FIG. 5B is an end view of the drag clutch of FIG. 5A.

FIG. 5A is an oblique view of a drag clutch 540. FIG. 5B is an end view of drag clutch 540. Drag clutch 540 is the same as first drag clutch 241 and second drag clutch 242.

In this example, drag clutch 540 is a hollow right circular cylindrical disk with a modified outer circumferential surface. Drag clutch 540 has a first side wall 541 and a second side wall 543. An outer circumferential surface of drag clutch 540 connects an outer edge 541_OE of first side wall 541 with an outer edge 543_OE of side wall 543. An inner circumferential surface 542 of drag clutch 540 connects an inner edge 541_IE of side wall 541 with an inner edge 543_IE of side wall 543

The outer circumferential surface of drag clutch has a first outer circumferential surface 544, and a release surface 547. First outer circumferential surface 544 extends clockwise around the outside of the perimeter of the disk from outer edge 544A to outer edge 544B, and is a portion of the outer circumferential surface. Outer edges 544B, 544A extend from outer edge 541_OE to outer edge 543_OE. Extending clockwise between outer edge 544B and outer edge 544A is release surface 547.

Drag clutch 540 also includes two substantially rectangular through slots 545, 546 that extend from first side wall 541 through drag clutch 540 to second side wall 543. Slots 545, 546 are sized so that clutch engagement tabs 352A, 352B, 452A, 452B fit within slots 545, 546 and when so positioned are engaged with drag clutch 540.

Figure 6:
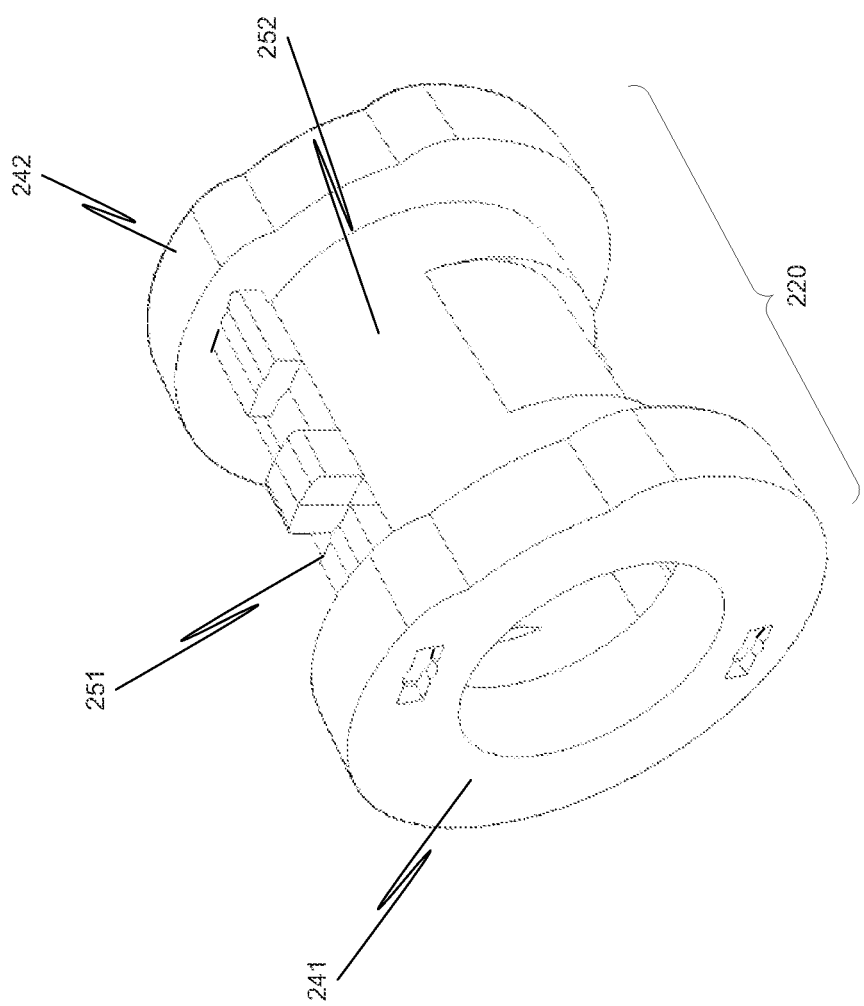
FIG. 6 is a close-up oblique of the rotation drive assembly.

FIG. 6 is an illustration of rotation drive assembly 220 with clutch engagement tabs 452A, 452B of second pawl 252 and clutch engagement tabs 352A, 352B (not visible) of first pawl 251 engaged with drag clutch 241 and drag clutch 242. The first pawl 251 is shown in it screw gear engaged position.

Each slot 545, 546 has a longitudinal axis 545L, 546L. Longitudinal axis 545L, 546L intersects centerline 540_CL of drag clutch 540 at an angle α. Angle α is less than or equal to eighty degrees. Drag clutch 540 is formed from an elastomeric material, and in one example is made of silicone rubber with a 70 to 80 Shore A Durometer. In another example, the elastomeric material is urethane with a 70 to 90 Shore A Durometer.

When rotation drive assembly 220 is considered to be engaged, one of drive pad 251T or drive pad 252T is in contact with drive rib 215. As an example, drive pad 252T is taken as in contact with drive rib 215. Prior to drive pad 252T contacting drive rib 215, drive rib 215 contacted ramp 252_R of second pawl 252. As housing 210 is rotated, rotational movement of the drag clutches 540, 241, 242 is resisted by the frictional drag of the clutches inner diameter on the top edge surface of inner legs (262A, 262B, 263A, and 263B), the internal frictional resistance exceeds the rotational torque needed to drive rib 215 to move up ramp 252_R and push second pawl 252 radially inward so that the plurality of gear teeth 456 (FIG. 4A) of second pawl 252 engages screw gear 130 as drive rib 215 moves onto contact surface 451_OC.

The radially inward force supplied by drive rib 215 on second pawl 252 on contact surface 451_OC is transferred by clutch engagement tabs 452A, 452B to drag clutches 241, 242. The radially inward force from engagement tabs 452A, 452B compresses drag clutches 241, 242.

Conversely, when drive pad 252T is not in contact with rib 215, drive rib 215 is not in contact with contact surface 451_OC of second pawl 252, and there in no radially inward force on second pawl 252 from rib 215. Consequently, drag clutches 241, 242 return to their original (relaxed or unengaged) states, because drag clutches 241, 242 are made from an elastomeric material. Angle α is selected so that in this original state, plurality of gear teeth 456 of second pawl 252 is dis-engaged from screw gear 130. This description also applies to pawl 251 and so is not repeated.

As noted above, the outer circumferential surface of drag clutch 540 includes a release surface 547. Starting at edge 544A and traversing the outer circumferential surface counterclockwise, releases surface 547 includes a first transition region 547A, a no contact region 547B, and a second transition region 547C.

As housing 210 is rotated in a first rotational direction around screw gear 130 and hence around drag clutch 540, a drag tab 217A, 217B on a rib 216, 213 (FIG. 2A) contacts first outer circumferential surface 544. The friction between the drag tab and first outer circumferential surface 544 provides feedback to the operator that assembly 105 is in the screw gear drive mode. However, housing 210 is rotated in the other rotational direction, the drag tab 217A, 217B passes over one of first and second transition regions 547A, 547C which reduces the friction and then moves to no contact region 547B. The change in frictional resistance notifies the operator that assembly 105 is disengaged from screw gear 130 and is in position to be slid along screw gear 130.

Housing

Figure 7A:
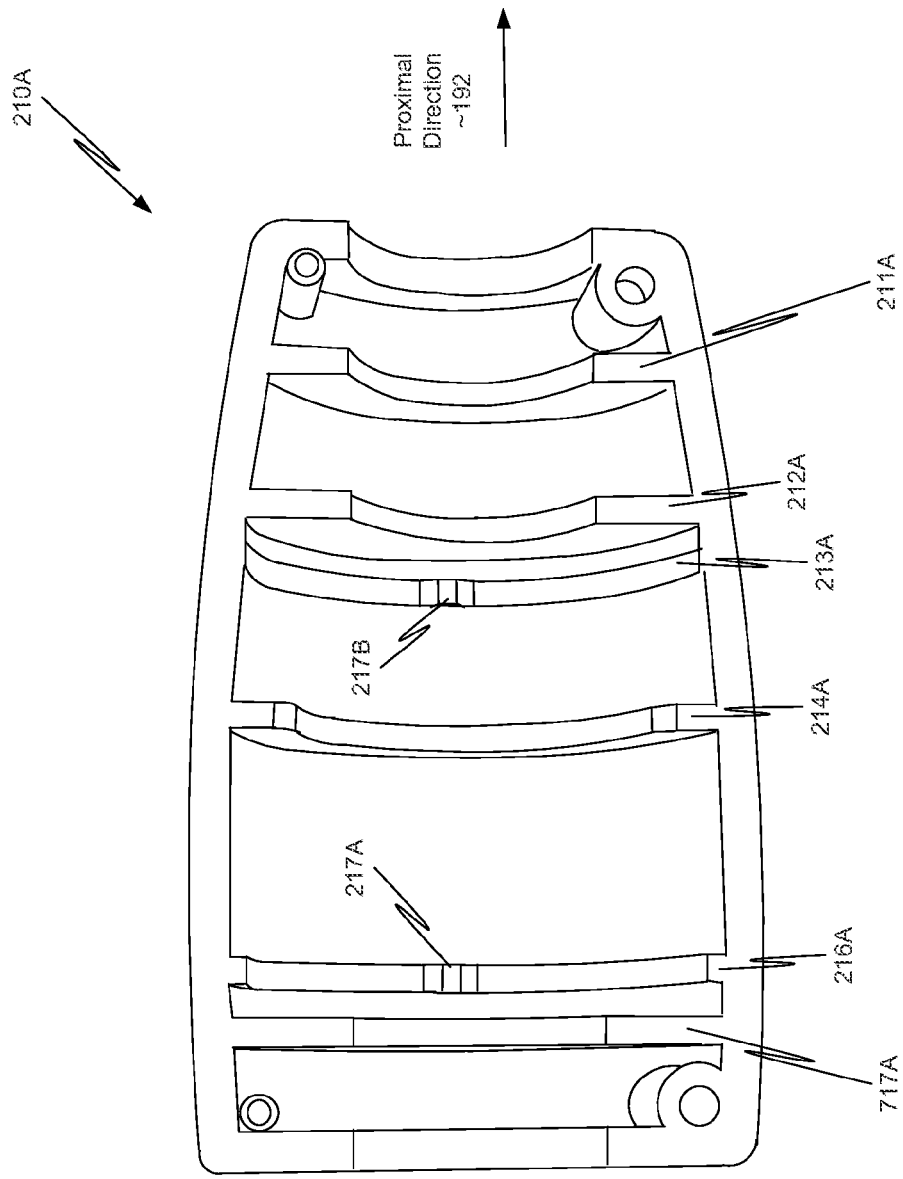
FIG. 7A is a view looking down into a first housing part.
Figure 7B:
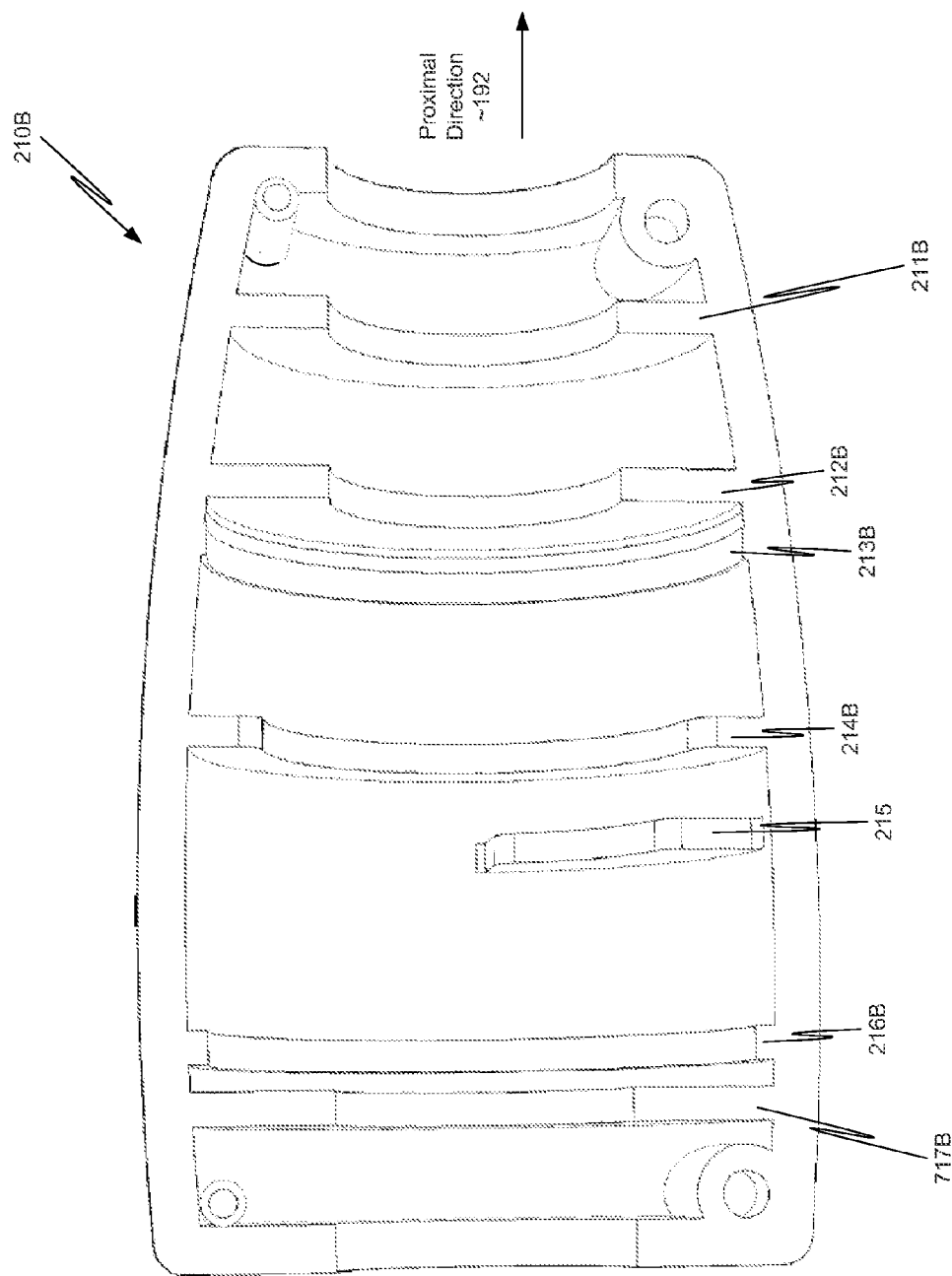
FIG. 7B is a view looking down into a second housing part.

FIG. 7A is a view looking down into first housing part 210A. FIG. 7B is a view looking down into second housing part 210B. In this example, first housing part 210A and second housing part 210B are joined using a post and hole arrangement. Ribs 212, 213, 214, 216, 717 extend around and from the inner circumferential surface of housing 210. Thus, ribs 212A, 212B, 213A, 213B, 214A, 214B, 216A, 216B, 717A, 717B in FIGS. 7A and 7B are each half of the corresponding rib in FIG. 2A.

Ribs 211 and 212 define longitudinal boundaries of a volume within housing 210 in which graft cover control engagement tabs 265A, 265B are constrained. The inner surface of rib 213 correlates with the longitudinal position and limits radially outward motion of the outer circumferential surface of drag clutch 242. The distal side of rib 212 acts a barrier to limit any longitudinal motion of drag clutch 242 in proximal direction 192.

Rib 214 limits the radially outward displacement of pawls 251, 252 when either or both of pawls 251, 252 are disengaged from screw gear 130. Drive rib 215 extends only partially around the inner circumferential surface of second housing part 210B, in this example, and so extends less than halfway around an inner surface of housing 210. The height of drive rib 215 from the inner circumferential surface of second housing part 210B is selected to engage pawls 251, 252, as described previously. The inner surface of rib 216 correlates with the longitudinal position and limits radially outward motion of the outer circumferential surface of drag clutch 241. The proximal side of rib 717 also acts as a barrier to limit any longitudinal motion of drag clutch 242 in distal direction 191.

Graft Cover Anchor

Figure 8:
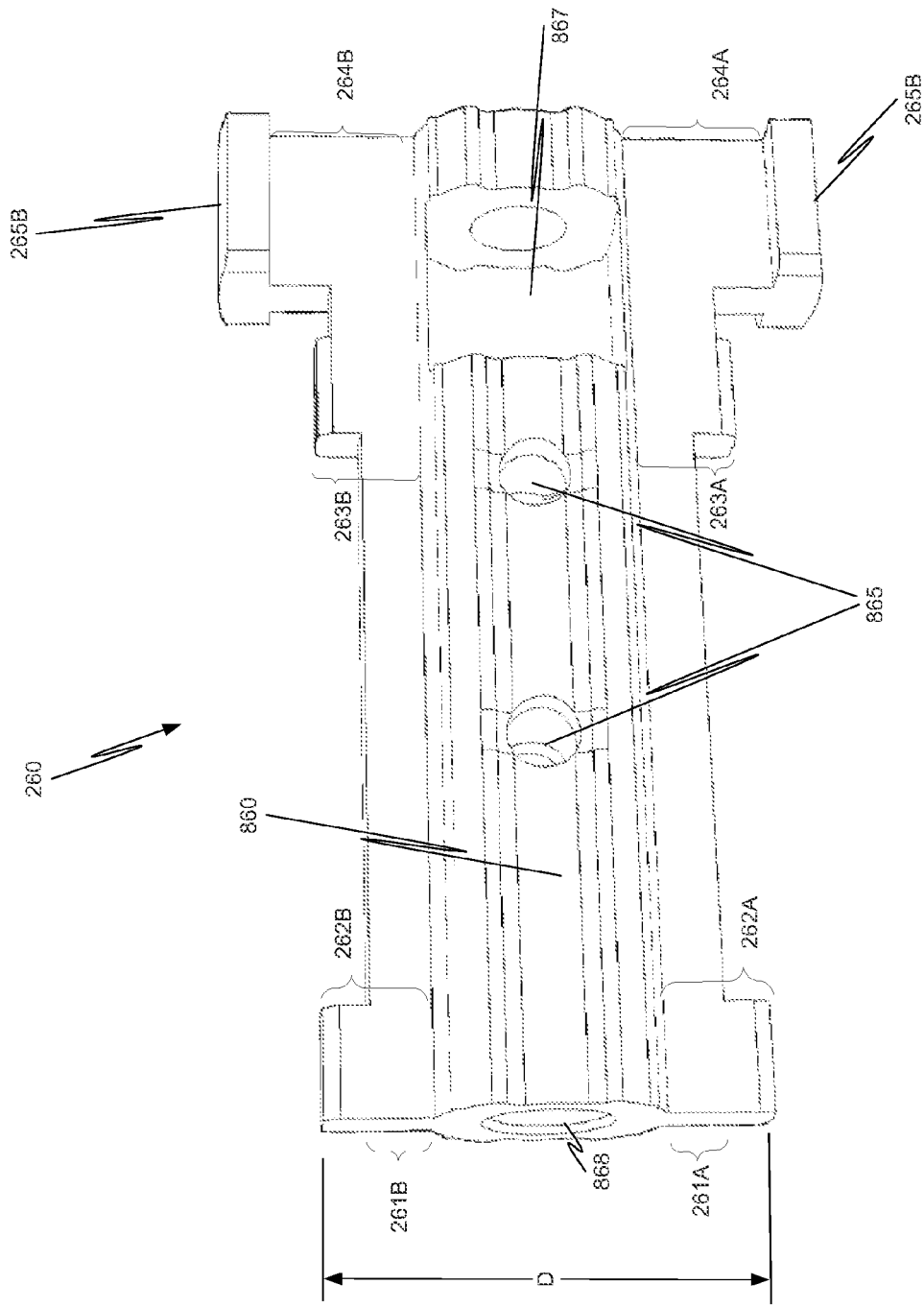
FIG. 8 is a close-up oblique view of a graft cover anchor.

FIG. 8 is an oblique view of one example of graft cover anchor 260. As described above, graft cover anchor 260 includes a first spacer 261A and a second spacer 262B extending longitudinally along, and from body 860. Graft cover anchor 260 also includes two sets of legs (262A, 262B), (263A, 263B). Each of legs 262A, 263A includes a portion of spacer 261A. Similarly, each of legs 262B, 263B includes a portion of spacer 261B.

The top edge surface of each leg in a set (262A, 262B), (263A, 263B) is rounded and distance D between the top edge surfaces of a set of legs is greater than the inner diameter of a drag clutch, as the drag clutch is mounted on the top edge surfaces of the set of legs.

Also, as described above, leg 264A extends from body 860 of graft cover anchor 260 to graft cover control engagement tab 265A. Leg 264B of graft cover anchor 260 extends from body 860 to graft cover control engagement tab 265B. Leg 264A includes a portion of spacer 261A, and leg 264B includes a portion of spacer 261B.

A center passage 868 extends through body 860 from a distal end surface of body 860 to a graft cover hemostatis seal cavity 867. A plurality of side holes 865 extends from an outer surface of body 860 to center passage 868. A graft cover is inserted into center passage 868 and is anchored to graft cover anchor 260 by glue inserted through plurality of side holes 865. A hemostatis seal is inserted in cavity 867.

The technique described for anchoring the graft cover to anchor 260 is illustrative only and is not intended to be limiting. Other graft cover anchors can be used having the characteristics described, except a different technique is used for securing the graft cover, sometimes referred to as a sheath, to the graft cover anchor.

Figure 9A:
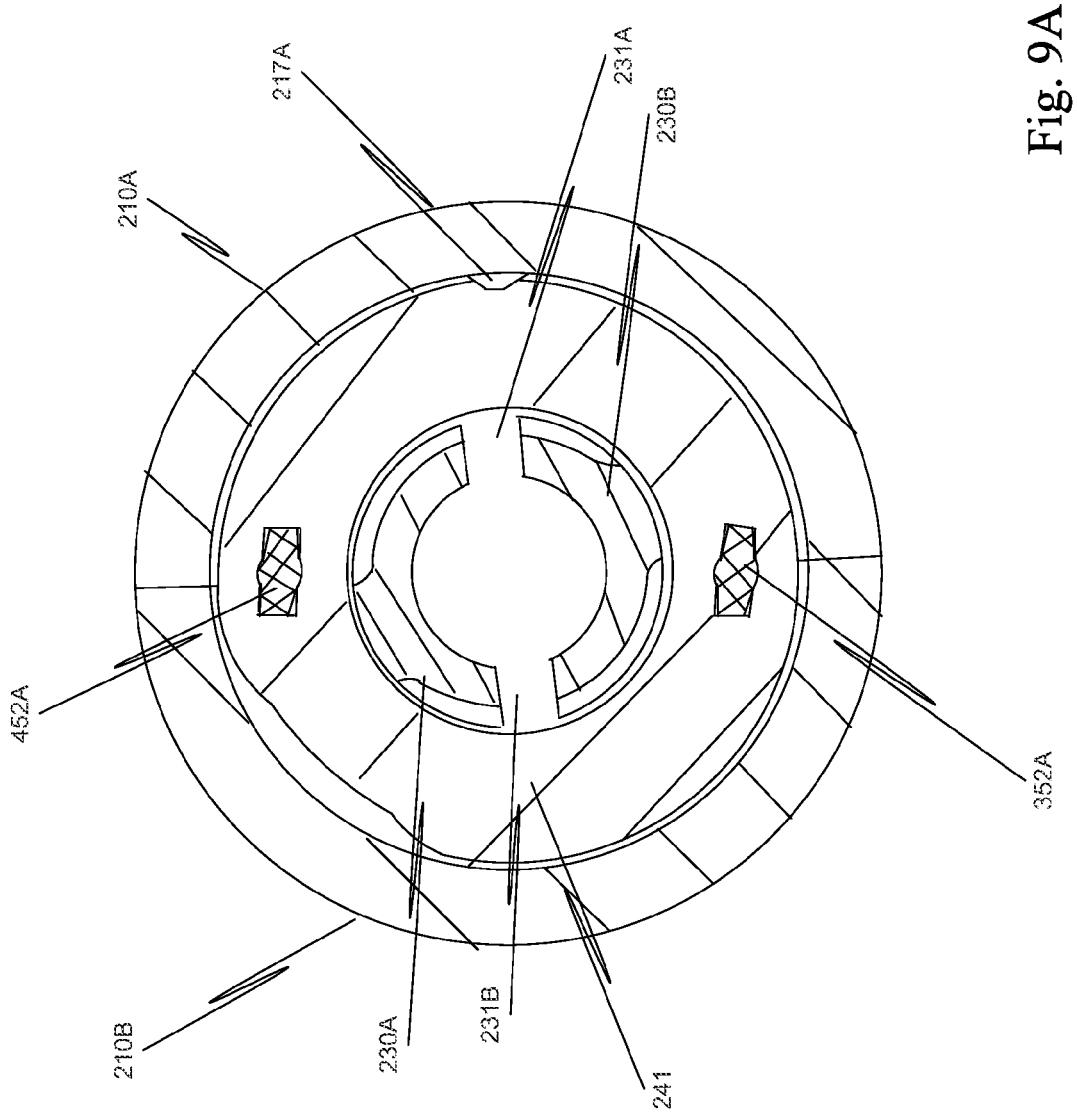
FIG. 9A is a side cross-sectional view of FIG. 2A taken at cut line 9A-9A after the housing has been rotated so that a drag tab is in contact with a drag clutch.
Figure 9B:
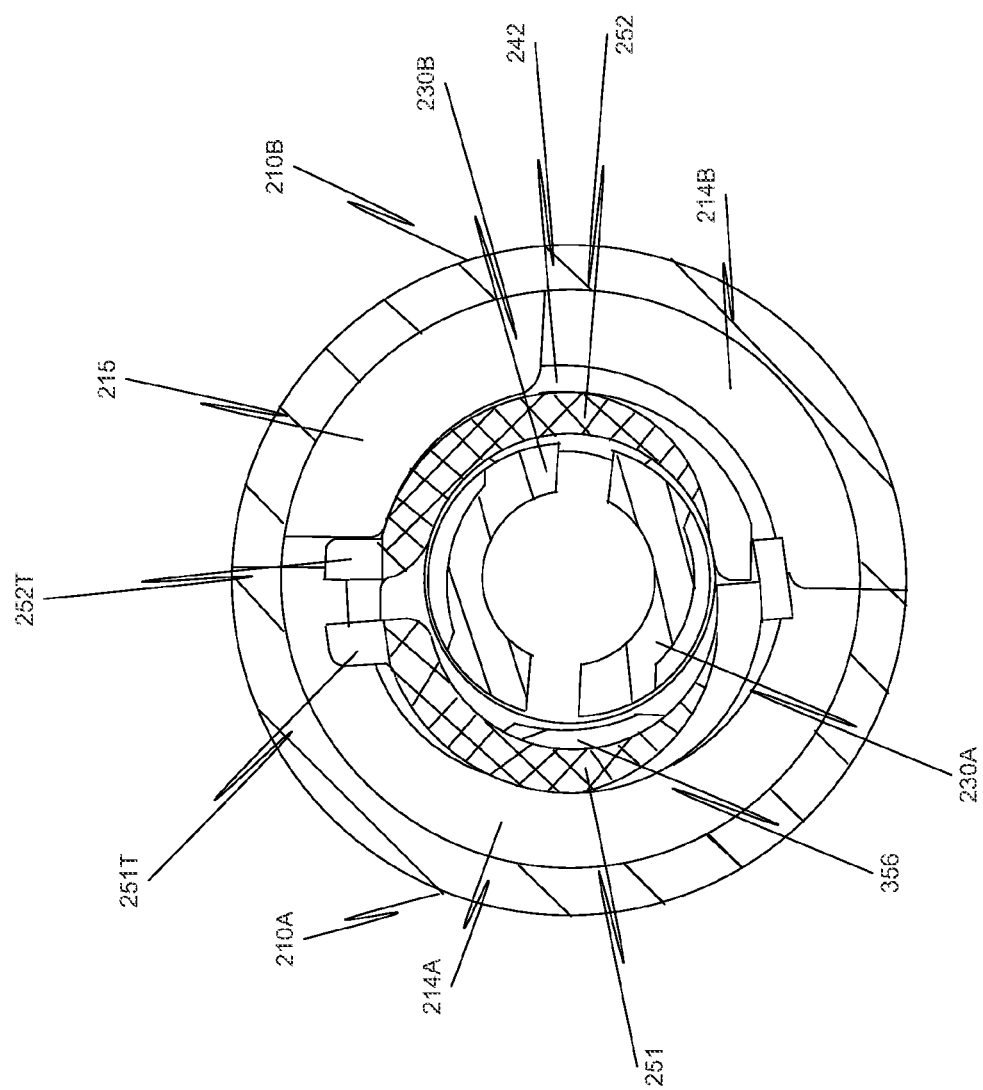
FIG. 9B is a side cross-sectional view of FIG. 2A taken at cut line 9C-9C after the housing has been rotated so that the drive rib is in contact with the drive pad of the pawl.
Figure 9C:
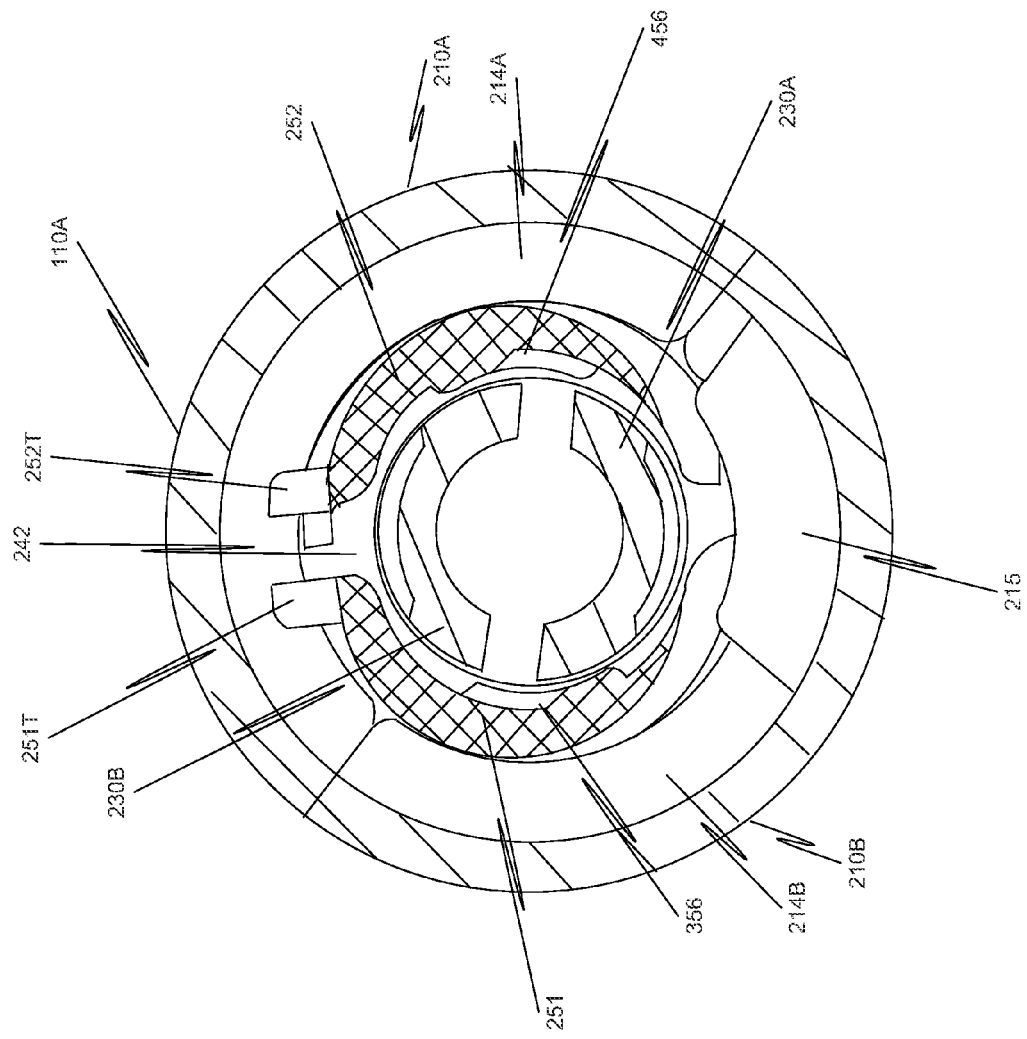
FIG. 9C is a side cross-sectional view of FIG. 2A taken at cut line 9C-9C.

FIG. 9A is a cross-sectional view along cut line 9A-9A in FIG. 2A after housing 210 has been rotated so that drag tab 217A is in contact with drag clutch 241. This illustration shows the two slots 231A and 231B between first screw gear part 230A and second screw gear part 230B. In FIGS. 9A to 9C, graft cover anchor 260 has been removed for clarity.

FIG. 9B is a side cross-sectional view along cut line 9C-9C in FIG. 2A after housing 210 has been rotated so that drive rib 215 is in contact with drive pad 252T of second pawl 252. Second pawl 252 is engaged with screw gear 130, while the plurality of gear teeth 356 of pawl 251 is disengaged from screw gear 130.

FIG. 9C is a side cross-sectional view along cut line 9C-9C in FIG. 2A. Drag tab 217 (not visible) is positioned over the release portion of outer circumferential surface of drag clutch 242 so that the user knows rotation drive assembly 220 is disengaged from screw gear 130. The drag clutches are not compressed and so the drag clutches orient pawl 251 and second pawl 252 so that both plurality of gear teeth 356 of pawl 251 and plurality of gear teeth 456 of second pawl 252 are disengaged from the screw gear and the outward radial motion is restrained by rib 214A, 214B. Thus, assembly 105 can be slid longitudinally along screw gear 130.

All examples and illustrative references are non-limiting and should not be used to limit the claims to specific implementations and embodiments described herein and their equivalents.

I claim:

1. A graft delivery system comprising:
    a graft cover retractor including:
    a screw gear including at least one longitudinal slot; and
    a drive and quick release assembly coupled to the screw gear,
    wherein the drive and quick release assembly slides along the at least one longitudinal slot to retract a graft cover affixed to the drive and quick release assembly;
    said drive and quick release assembly rotates in a first rotational direction about the screw gear to retract the graft cover using the screw gear; and
    said drive and quick release assembly transitions from rotating to sliding by rotating the drive and quick release assembly a fraction of a complete revolution in a second rotation direction that is opposite to the first rotation direction being used to retract the graft cover.

2. The graft delivery system of claim 1, wherein the drive and quick release assembly rotates in the second rotational about the screw gear to move the graft cover in a distal direction.

3. The graft delivery system of claim 1, wherein the drive and quick release assembly further comprises:
   a housing; and
   a drive mechanism mounted in the housing, wherein the drive mechanism engages with the screw gear upon the housing being rotated a predetermined fraction of a revolution in one of the first rotational direction and the second rotational direction, and continues to engage the screw gear until the housing is rotated in the other of the first rotational direction and the second rotational direction.

4. The graft delivery system of claim 3, wherein the drive mechanism comprises:
   a graft cover anchor, mounted within the housing, including:
   a body;
   at least one graft cover control engagement tab positioned outside the screw gear;
   a leg extending from the at least one graft cover control engagement tab through the at least one longitudinal slot in the screw gear to the body of the graft cover anchor; and
   a rotation drive assembly mounted in the housing,
   wherein the rotation drive assembly, following engagement with the screw gear and continued rotation of the housing, moves the housing along the screw gear, which in turn moves the graft cover anchor longitudinally; and
   said rotation drive assembly releases engagement with the screw gear following the housing being rotated in the other of the first direction and the second direction; and
   longitudinal motion of the housing along the screw gear, following the housing being rotated in the other of the first direction and the second direction, moves the graft cover anchor longitudinally.

5. The graft delivery system of claim 4 wherein the rotation drive assembly comprises:
   a plurality of pawls, wherein each pawl in the plurality comprises:
   an inner surface including a plurality of gear teeth for engaging with the screw gear.

6. The graft delivery system of claim 5 wherein each pawl includes an outer surface having a ramp surface.

7. The graft delivery system of claim 5 wherein each pawl in the plurality includes a drive pad.

8. The graft delivery system of claim 7, wherein housing further comprises:
   a drive rib,
   wherein the plurality of gear teeth of one pawl in the plurality of pawls engages the screw gear when the drive pad of the one pawl is in contact with the drive rib; and
   said plurality of gear teeth of the one pawl is disengaged from the screw gear when the drive rib is not in contact with an outer surface of the one pawl.

9. The graft delivery system of claim 3, wherein the drive mechanism comprises:
   a rotation drive assembly, mounted in the housing,
   a first drag clutch;
   a second drag clutch;
   a first pawl operatively mounted in the first drag clutch and the second drag clutch; and
   a second pawl operatively mounted in the first drag clutch and the second drag clutch.

10. The graft delivery system of claim 9 wherein the first drag clutch further comprises:
    a first side surface;
    a second side surface, removed from the first side surface; and
    an outer surface connecting the first side surface to the second side surface, wherein the outer surface includes a release surface.

11. The graft delivery system of claim 10 wherein the release surface comprises:
    a transition surface; and
    a no contact surface.

12. The graft delivery system of claim 10 wherein the first drag clutch further comprises:
    a slot, extending through the first draft clutch from the first side surface to the second side surface, having a longitudinal axis,
    wherein the longitudinal axis forms an angle with a center line of the first drag clutch; and
    the angle is less than eighty degrees.

13. The graft delivery system of claim 10 where the first drag clutch and the second drag clutch are made of an elastomeric material.

14. The graft delivery system of claim 10 the first pawl comprises:
    an inner surface including a plurality of gear teeth for engaging with the screw gear.

15. The graft delivery system of claim 14 wherein the first pawl includes a drive pad.

16. The graft delivery system of claim 15, wherein housing further comprises:
    a drive rib,
    wherein the plurality of gear teeth engages the screw gear when the drive pad is in contact with the drive rib; and
    said plurality of gear teeth is disengaged from the screw gear when the drive rib is not in contact with an outer surface of the first pawl.

17. The graft delivery system of claim 16 wherein the drive rib extends less than halfway around an inner surface of the housing.

18. The graft delivery system of claim 10 wherein the first pawl includes an outer surface having a ramp surface.

* * * * *